United States Patent
Lee (10) Patent No.: US 12,180,506 B2
(45) Date of Patent: Dec. 31, 2024

(54) METHODS FOR PROMOTING PROLIFERATION AND PROPAGATION OF STEM CELLS

(71) Applicant: MYCOMAGIC BIOTECHNOLOGY CO., LTD., New Taipei (TW)

(72) Inventor: Michael Lee, Taipei (TW)

(73) Assignee: MYCOMAGIC BIOTECHNOLOGY CO., LTD., New Taipei (TW)

( * ) Notice: Subject to any disclaimer, the term of this patent is extended or adjusted under 35 U.S.C. 154(b) by 470 days.

(21) Appl. No.: 17/235,777

(22) Filed: Apr. 20, 2021

(65) Prior Publication Data

US 2022/0106569 A1 Apr. 7, 2022

Related U.S. Application Data (60) Provisional application No. 63/087,677, filed on Oct. 5, 2020.

(51) Int. Cl.
 *C12N 5/0775* (2010.01)
(52) U.S. Cl.
 CPC ......... *C12N 5/0667* (2013.01); *C12N 5/0663* (2013.01); *C12N 2501/998* (2013.01)
(58) Field of Classification Search
 None
 See application file for complete search history.

(56) References Cited

U.S. PATENT DOCUMENTS

| | | |
|---|---|---|
| 7,601,808 B2 | 10/2009 | Lin |
| 9,018,171 B2 | 4/2015 | Ko |
| 9,528,093 B2 | 12/2016 | Lyu |
| 9,937,226 B2 | 4/2018 | Yu |
| 9,975,931 B2 | 5/2018 | Chao |
| 2016/0184389 A1 | 6/2016 | Yu |
| 2019/0091286 A1 | 3/2019 | Yu |
| 2019/0298794 A1 | 10/2019 | Chao |

OTHER PUBLICATIONS

Extended European Search Report issued in European Patent Application No. 21201019.3 on Feb. 21, 2022.
Lotz, Steven et al., "Sustained Levels of FGF2 Maintain Undifferentiated Stem Cell Cultures with Biweekly Feeding," PLoS One, vol. 8, No. 2, p. e56289, XP055086481. 10 pages.
Qu, Zheng-Wei et al., "Recombinant Expression and Bioactivity Comparison of Four Typical Fungal Immunomodulatory Proteins from Three Main Ganoderma Species," BMC Biotechnology, (2018), vol. 18, No. 80, XP055889048, DOI: 10.1186/s12896-018-0488-0.

*Primary Examiner* — Teresa E Knight
(74) *Attorney, Agent, or Firm* — Prosyla Group PC (57) ABSTRACT

The present disclosure provides a method for proliferating or propagating undifferentiated stem cells, comprising contacting a population of stem cells with an effective amount of *Ganoderma* immunomodulatory protein or a recombinant thereof or a fragment thereof.

12 Claims, 10 Drawing Sheets

Specification includes a Sequence Listing.

SEQUENCE LISTING

```
<160> NUMBER OF SEQ ID NOS: 4

<210> SEQ ID NO 1
<211> LENGTH: 6
<212> TYPE: PRT
<213> ORGANISM: Ganoderma microsporum

<400> SEQUENCE: 1

Leu Ala Trp Asn Val Lys
1               5

<210> SEQ ID NO 2
<211> LENGTH: 10
<212> TYPE: PRT
<213> ORGANISM: Ganoderma microsporum

<400> SEQUENCE: 2

Asp Leu Gly Val Arg Pro Ser Tyr Ala Val
1               5                   10

<210> SEQ ID NO 3
<211> LENGTH: 111
<212> TYPE: PRT
<213> ORGANISM: Ganoderma microsporum

<400> SEQUENCE: 3

Met Ser Asp Thr Ala Leu Ile Phe Thr Leu Ala Trp Asn Val Lys Gln
1               5                   10                  15

Leu Ala Phe Asp Tyr Thr Pro Asn Trp Gly Arg Gly Arg Pro Ser Ser
            20                  25                  30

Phe Ile Asp Thr Val Thr Phe Pro Thr Val Leu Thr Asp Lys Ala Tyr
        35                  40                  45

Thr Tyr Arg Val Val Val Ser Gly Lys Asp Leu Gly Val Arg Pro Ser
    50                  55                  60

Tyr Ala Val Glu Ser Asp Gly Ser Gln Lys Ile Asn Phe Leu Glu Tyr
65                  70                  75                  80

Asn Ser Gly Tyr Gly Ile Ala Asp Thr Asn Thr Ile Gln Val Tyr Val
                85                  90                  95

Ile Asp Pro Asp Thr Gly Asn Asn Phe Ile Val Ala Gln Trp Asn
            100                 105                 110

<210> SEQ ID NO 4
<211> LENGTH: 140
<212> TYPE: PRT
<213> ORGANISM: Artificial Sequence
<220> FEATURE:
<223> OTHER INFORMATION: recombinant protein

<400> SEQUENCE: 4

Glu Ala Glu Ala Glu Phe Met Ser Asp Thr Ala Leu Ile Phe Thr Leu
1               5                   10                  15

Ala Trp Asn Val Lys Gln Leu Ala Phe Asp Tyr Thr Pro Asn Trp Gly
            20                  25                  30

Arg Gly Arg Pro Ser Ser Phe Ile Asp Thr Val Thr Phe Pro Thr Val
        35                  40                  45

Leu Thr Asp Lys Ala Tyr Thr Tyr Arg Val Val Val Ser Gly Lys Asp
    50                  55                  60

Leu Gly Val Arg Pro Ser Tyr Ala Val Glu Ser Asp Gly Ser Gln Lys
65                  70                  75                  80

Ile Asn Phe Leu Glu Tyr Asn Ser Gly Tyr Gly Ile Ala Asp Thr Asn
```

-continued

```
                85                      90                      95

Thr Ile Gln Val Tyr Val Ile Asp Pro Asp Thr Gly Asn Asn Phe Ile
            100                     105                 110

Val Ala Gln Trp Asn Tyr Leu Glu Gln Lys Leu Ile Ser Glu Glu Asp
        115                     120                 125

Leu Asn Ser Ala Val Asp His His His His His His
130                     135                 140
```

METHODS FOR PROMOTING PROLIFERATION AND PROPAGATION OF STEM CELLS

This application claims benefit of U.S. Provisional Application No. 63/087,677, filed Oct. 5, 2020, under 35 U.S.C. § 119. The entire content of the prior application is herein incorporated by reference.

The instant application contains a Sequence Listing which has been filed electronically in ASCII format and is hereby incorporated by reference in its entirety. Said ASCII copy, created on Apr. 20, 2021, is named G4590-10300US_Seq-Listing.txt and is 3 kilobytes in size.

FIELD OF THE INVENTION

The present disclosure relates to a method for promoting proliferation of stem cells. Particularly, the present disclosure provides a method of using an immunomodulatory protein to promote proliferation of stem cells.

BACKGROUND OF THE INVENTION

Pluripotent stem cells are characterized by the ability to self-replicate and differentiate. Stem cells are characterized typically by morphology as well as the presence of characteristic markers. Stem cell differentiation can result in a phenotypic change in cell morphology. Stem cell differentiation can also result in a loss of stem cell markers or telomerase activity. Stem cell differentiation can further result in acquiring markers- or morphologies characteristic of one or more of the three embryonic germ layers-ectoderm, mesoderm or endoderm. Currently, culture reagents that eliminate differentiated cells and promote expansion of undifferentiated cells are used to propagate undifferentiated pluripotent stem cells.

However, there is a need in the art to develop a method of promoting expansion of undifferentiated stem cells.

SUMMARY OF THE INVENTION

The present disclosure surprisingly found that *Ganoderma* immunomodulatory protein or a recombinant thereof provides advantageous efficacy in proliferating or propagating undifferentiated stem cells and maintaining the stem cells undifferentiated.

In one aspect, the present disclosure provides a method for proliferating or propagating undifferentiated stem cells, comprising contacting a population of stem cells with an effective amount of *Ganoderma* immunomodulatory protein, a recombinant thereof or a fragment thereof.

In another aspect, the present disclosure also provides a stem cell culture supplement, comprising *Ganoderma* immunomodulatory protein, a recombinant thereof or a fragment thereof in an amount sufficient to proliferate or propagate undifferentiated stem cells and a chemically defined stem cell culture medium.

In one embodiment, the stem cells described herein maintain undifferentiated.

In one embodiment, the *Ganoderma* immunomodulatory protein or a recombinant thereof described herein comprises an amino acid sequence of SEQ ID NO: 3. In one embodiment, the recombinant of *Ganoderma* immunomodulatory protein comprises an amino acid sequence of SEQ ID NO: 4. In one embodiment, the fragment of *Ganoderma* immunomodulatory protein comprises an amino acid sequence selected from the group consisting of SEQ ID NOs: 1 to 2.

The sequences of SEQ ID NO: 1 to 4 are listed as follows.

```
                                           (SEQ ID NO: 1)
LAWNVK (SEQ ID NO: 2)
DLGVRPSYAV (SEQ ID NO: 3)
MSDTALIFTLAWNVKQLAFDYTPNW

GRGRPSSFIDTVTFPTVLTDKAYTY

RVVVSGKDLGVRPSYAVESDGSQKI

NFLEYNSGYGIADTNTIQVYVIDPD

TGNNFIVAQWN (SEQ ID NO: 4)
EAEAEFMSDTALIFTLAWNVKQLAF

DYTPNWGRGRPSSFIDTVTFPTVLT

DKAYTYRVVVSGKDLGVRPSYAVES

DGSQKINFLEYNSGYGIADTNTIQV

YVIDPDTGNNFIVAQWNYLEQKLIS

EEDLNSAVDHHHHHH
```

In one embodiment, the amount of the *Ganoderma* immunomodulatory protein or the recombinant or fragment thereof is less than 15 μg/mL; preferably, less than 12.5 μg/mL. In some embodiment, the amount of the *Ganoderma* immunomodulatory protein or the recombinant or fragment thereof ranges from about 1.0 μg/mL to about 15 μg/mL, about 1.5 μg/mL to about 15 μg/mL, about 2.0 μg/mL to about 15 μg/mL, about 2.5 μg/mL to about 15 μg/mL, about 3.0 μg/mL to about 15 μg/mL, about 3.5 μg/mL to about 15 μg/mL, about 4.0 μg/mL to about 15 μg/mL, about 4.5 μg/mL to about 15 μg/mL, about 5.0 μg/mL to about 15 μg/mL, about 5.5 μg/mL to about 15 μg/mL, about 6.0 μg/mL to about 15 μg/mL, about 6.5 μg/mL to about 15 μg/mL, about 7.0 μg/mL to about 15 μg/mL, about 7.5 μg/mL to about 15 μg/mL, about 8.0 μg/mL to about 15 μg/mL, about 8.5 μg/mL to about 15 μg/mL, about 9.0 μg/mL to about 15 μg/mL, about 9.5 μg/mL to about 15 μg/mL, about 10.0 μg/mL to about 15 μg/mL, about 10.5 μg/mL to about 15 μg/mL, about 11.0 μg/mL to about 15 μg/mL, about 11.5 μg/mL to about 15 μg/mL, 1.0 μg/mL to about 12.5 μg/mL, about 1.5 μg/mL to about 12.5 μg/mL, about 2.0 μg/mL to about 12.5 μg/mL, about 2.5 μg/mL to about 12.5 μg/mL, about 3.0 μg/mL to about 12.5 μg/mL, about 3.5 μg/mL to about 12.5 μg/mL, about 4.0 μg/mL to about 12.5 μg/mL, about 4.5 μg/mL to about 12.5 μg/mL, about 5.0 μg/mL to about 12.5 μg/mL, about 5.5 μg/mL to about 12.5 μg/mL, about 6.0 μg/mL to about 12.5 μg/mL, about 6.5 μg/mL to about 12.5 μg/mL, about 7.0 μg/mL to about 12.5 μg/mL, about 7.5 μg/mL to about 12.5 μg/mL, about 8.0 μg/mL to about 12.5 μg/mL, about 1.5 μg/mL to about μg/mL, about 1.5 μg/mL to about 8.5 μg/mL, about 1.5 μg/mL to about 8.0 μg/mL, about 1.5 μg/mL to about 7.5 μg/mL, about 1.5 μg/mL to about 7.0 μg/mL, about 1.5 μg/mL to about 6.5 μg/mL, about 1.5 μg/mL to about 6.0 μg/mL. In a further embodiment, the amount of the *Ganoderma* immunomodulatory protein or the recombinant or fragment thereof is about 1.5 μg/mL, about 1.5625 μg/mL, about 3.0 μg/mL, about 3.125 μg/mL, about 6.25 μg/mL or about 12.5 μg/mL.

In one embodiment, the population of the stem cells is of human origin.

In one embodiment, the population of the stem cells comprises a population of induced pluripotent stem (iPS) cells, a population of embryonic stem (ES) cells, a population of germinal cells, a population of tissue-specific stem cells, or a population of adult stem cells. In some embodiments, the stem cells are embryonic stem cells, mesenchymal stem cells (MSC), marrow stromal cells, hematopoietic stem cells, adipose-derived stem cells, endothelial stem cells, dental pulp stem cells, or neural stem cells.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein for reference.

In this application, the use of the singular includes the plural, the article "a" or "an" means "at least one," and the use of "or" means "and/or," unless specifically stated otherwise.

As used herein, "growth" refers to a process of becoming larger, longer, or more numerous, or an increase in size, number, or volume.

As used herein, "differentiation" refers to the process of development with an increase in the level of organization or complexity of a cell or tissue, accompanied with a more specialized function.

As used herein, "effective amount" means an amount sufficient to propagate undifferentiated stem cells and maintain the stem cells undifferentiated.

As used herein, "subject" refers to either a human or non-human animal.

As used herein, "pluripotent stem cells" refers to cells that can differentiate into all the cells of the three embryonic germ layers forming the body organs, nervous system, skin, muscle and skeleton, but not embryonic components of the trophoblast and placenta.

As used herein, "stem cells" refers to undifferentiated cells having high proliferative potential with the ability to self-renew (make more stem cells by cell division) that can generate daughter cells that can undergo terminal differentiation into more than one distinct cell phenotype.

As used herein, "proliferation" refers to a process by which a cell grows and divides to produce daughter cells, and the daughter cells have the same phenotype to the cell.

As used herein, "propagation" refers to expansion of a population of cells by the continuous division of single cells into identical daughter cells.

As used herein, "cell culture" or "culture" refers to the maintenance of cells in an artificial (e.g., an in vitro) environment.

As used herein, "cell culture medium," "culture medium," or "medium" (and in each case plural media) refer to a nutritive composition that supports the cultivation and/or growth of cells.

A "chemically defined medium" refers to a growth medium suitable for the in vitro or ex vivo cell culture of human or animal cells in which all of the chemical components are known. In a particular embodiment, a chemically defined medium is entirely free of animal-derived components and does not contain either fetal bovine serum, bovine serum albumin or human serum albumin as these products are derived from bovine or human sources and contain complex mixes of albumins and lipids.

It is surprisingly found that culturing stem cells with *Ganoderma* immunomodulatory protein or the recombinant or fragment thereof can proliferate or propagate the stem cells but not differentiate them. That is, the *Ganoderma* immunomodulatory protein or the recombinant or fragment thereof can proliferate or propagate undifferentiated stem cells and maintain them undifferentiated in several passages. The resulting undifferentiated stem cells are multipotent or pluripotent.

Accordingly, the present disclosure provides a method for proliferating or propagating undifferentiated stem cells, comprising contacting a population of stem cells with an effective amount of *Ganoderma* immunomodulatory protein or a recombinant thereof or a fragment thereof.

The Certain embodiments of the stem cells include embryonic stem cells, mesenchymal stem cells (MSC), marrow stromal cells, hematopoietic stem cells, adipose-derived stem cells, endothelial stem cells, dental pulp stem cells, and neural stem cells. A particular embodiment of the engineered stem cell is MSC.

The preparation of the *Ganoderma* immunomodulatory protein or the recombinant or fragment thereof has been described in U.S. Pat. No. 7,601,808. Particularly, the *Ganoderma* immunomodulatory protein is referred to as GMI; the recombinant of *Ganoderma* immunomodulatory protein is referred to as reGMI; and the fragment of *Ganoderma* immunomodulatory protein is referred to as SEQ ID NOs: 2 and 3 in U.S. Pat. No. 7,601,808. The *Ganoderma* immunomodulatory protein or the recombinant or fragment thereof is in an amount less than 15 µg/mL, preferably 12.5 µg/mL.

The *Ganoderma* immunomodulatory protein or the recombinant or fragment thereof can be added to chemically defined stem cell media comprising essential mineral nutrients, essential salts, essential amino acids, one or more supplements and hyaluronan. Exemplary commercial media include classic formulations such as DMEM, DMEM:F12, RPMI, and or modifications thereof.

Also, the present disclosure provides a stem cell culture supplement, comprising *Ganoderma* immunomodulatory protein, a recombinant thereof or a fragment thereof in an amount sufficient to proliferate or propagate undifferentiated stem cells and a chemically defined cell culture medium.

The chemically defined cell culture medium is known in the art for in vitro culturing of stem cells. *Ganoderma* immunomodulatory protein, a recombinant thereof or a fragment thereof can be added to the chemically defined cell culture medium to proliferate or propagate undifferentiated stem cells and a chemically defined stem cell culture medium.

The culture media may be used in all cell processing steps including, cryopreserving, thawing, resuspension, modulating, expanding, or maintaining cell populations, particularly populations of cells comprising hematopoietic stem cells.

Cells supported by the culture medium described herein can be cultivated according to the experimental conditions determined by the investigator. It is to be understood, however, that the optimal plating and culture conditions for a given animal cell type can be determined by one of ordinary skill in the art using only routine experimentation.

The following examples are offered to illustrate but not limit the claimed invention.

EXAMPLES

Materials and Methods

Cultivation of Human Bone Marrow-Derived and Adipose Tissue-Derived Mesenchymal Stem Cells Bone marrow-derived mesenchymal stem cells (BMSCs) extracted from the bone marrow of 56-year-old donor and tissue-derived mesenchymal stem cells were obtained from ATCC (Manassas, VA, USA). Adipose-derived stem cells (ADSCs) were purchased from Lonza. ADSCs were seeded into 10 cm petri-dish with mesenchymal stem cell basal medium (American Type Culture Collection, ATCC) containing MSC supplement (2% FBS, 5 ng/ml rhFGF basic, 5 ng/ml rhFGF acidic and 5 ng/ml EGF) and L-Alanyl-L-Glutamine (2.4 mM). BMSCs were seeded in 10 cm petri-dish with mesenchymal stem cell growth kit (ATCC) containing 7% FBS, 15 ng/ml rhIGF-1, 125 pg/ml rhFGF-b and L-Alanyl-L-Glutamine (2.4 mM). Culture media were changed at 24 h post-seeding and every 3 days thereafter. When reaching confluence, cells were detached by using 0.15% trypsin at 37° C. for 4 min, and collected cells were passaged at the initial cell seeding density every 10 days. Cell morphology was recorded by using phase contrast microscope.

MSCs Proliferation

ADSCs ($5 \times 10^5$ cells) and BMSCs ($2 \times 10^5$ cells) were seeded in 10 cm petri-dish for 24 h and then treated with different concentration of GMI (0, 1, 3 and 5 µg/ml) for 72 h. After treatment, cells were washed with DPBS twice and incubated with 1 ml accutase at 37° C. for 5 min. After incubation, cells were collected and washed with DPBS. Finally, total cell number was counted by a hemocytometer.

Flow Cytometry Analysis

Control MSCs and GMI-treated MSCs harvested from different passages were assessed for cell surface marker expression by flow cytometry. Briefly, cells were collected, washed with DPBS and incubated with nonspecific blocking solution containing 1% bovine serum albumin for 30 min. After blocking, cells were washed with DPBS and centrifuged to remove the blocking solution. Then, cells were incubated with fluorescence-conjugated anti-human antibodies for 45 min. Specifically, antibodies against CD29 (557332), CD106 (563525), CD146 (563619) and CD166 (565461) were purchased from BD Pharmingen; Human MSC analysis Kit (562245) was also purchased from BD Pharmingen. Antibodies against mouse IgG were used as negative staining isotype control. Stained MSCs were resuspended in DPBS and further analyzed by using flow cytometry (BD Accuri™ C6 Plus).

MSCs Adipogenic and Osteogenic Differentiation

To evaluate whether GMI treatment affects the differentiation potential of MSCs, cells were seeded and incubated with mesenchymal stem cell growth kit (ATCC) plus different concentration of GMI in 10 cm petri-dish for 3 days as previously described. After GMI treatment, cells were harvested and seeded into a 24-well plate for adipogenic and osteogenic differentiation assay. Adipogenic and osteogenic differentiation assay were performed by using Mesenchymal Stem Cell Adipogenesis Kit and Mesenchymal Stem Cell Osteogenesis Kit (EMD Millipore Corp., MA, USA), respectively. In adipogenic differentiation condition, cells were treated with adipogenic induction media containing 1 mM dexamethasone, 0.5 mM IBMX, 10 µg/ml insulin and 100 mM indomethacin. In osteogenic differentiation condition, cells were treated with osteogenic induction media containing 0.1 mM dexamethasone, 0.2 mM ascorbic acid 2-phosphate, and 10 mM glycerol 2-phosphate. When the cells were 100% confluent, the medium was carefully aspirated from each well and 0.5 ml Adipogenesis Induction medium or Osteogenesis Induction medium was added. WHAT was replaced with fresh induction medium every 2-3 days. BMSCs could differentiate into adipocyte or osteocyte after 21 days or 14 days of induction. MSCs differentiation was further analyzed by the following experiments.

Histological Staining

In adipogenic differentiation assay, the medium was carefully aspirated from each well and then adipocyte was fixed by 4% paraformaldehyde for 30 min at room temperature. After fixation, each well was rinsed three times with PBS and then rinsed with water twice. Enough Oil Red O solution (0.4 ml/well) was added to each well. Then, the plate was incubated at room temperature for 50 min. After incubation, the Oil Red O solution was removed and the well was rinsed three times with 1 ml water. Hematoxylin solution (0.4 ml/well) was used to stain cell nucleus for 5 min. Finally, the results were observed by microscope and photographed under a light microscope (magnification, ×400). In osteogenic differentiation assay, the medium was carefully aspirated from each well and osteocyte was fixed by incubation in ice-cold 70% ethanol for 1 hour at room temperature. After fixation, the ethanol was carefully aspirated and rinsed twice with water for 5 min. The water was aspirated and enough Alizarin Red Solution was added to cover the well (0.5 ml/well), which was then incubated at room temperature for 30 min. After incubation, the Alizarin Red Solution was removed and the well was washed four times with 1 ml water. Then, 1 ml water was added to each well to prevent the cells from drying. Finally, the results were observed by microscope and photographed under a light microscope (magnification, ×100).

Statistical Analysis

Statistical data are presented as mean±SEM. Statistical analysis was performed by Student's t test for comparison between two groups with significance set at a p value of less than 0.05.

Example 1

Low Dose GMI Treatment Induces ADSC Proliferation

Figure 1A:
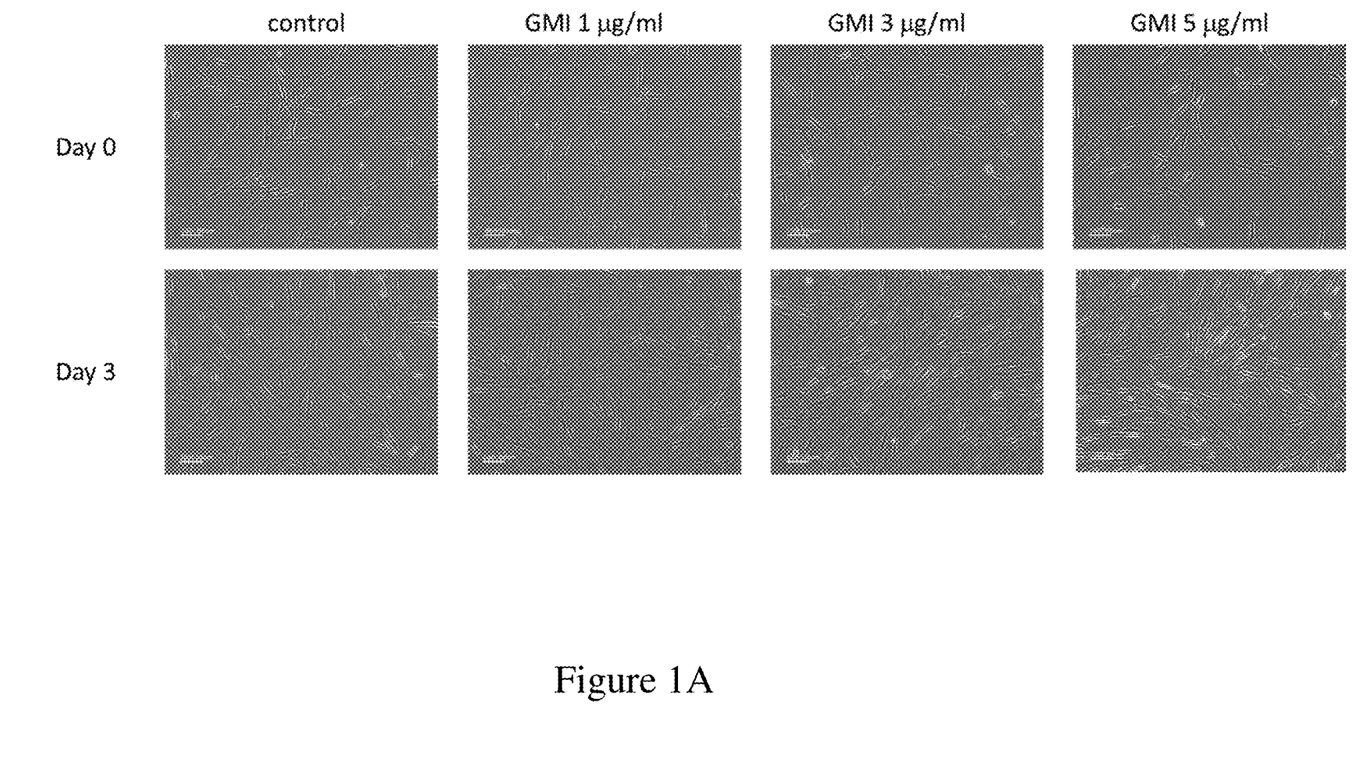
FIGS. 1A and 1B show the effect of GMI on ADSC proliferation. ADSCs ($5\times10^5$ cells) were treated with different concentrations of GMI (0, 1, 3 and 5 µg/ml) for 3 days. After treatment, cells were harvested, and total cell number was analyzed by a hemocytometer (B). Phase contrast images (A) were photographed by a light microscope. The experiments were performed in triplicate (n=3). p<0.01 and *p<0.001, versus control cell with no GMI treatment.
Figure 1B:
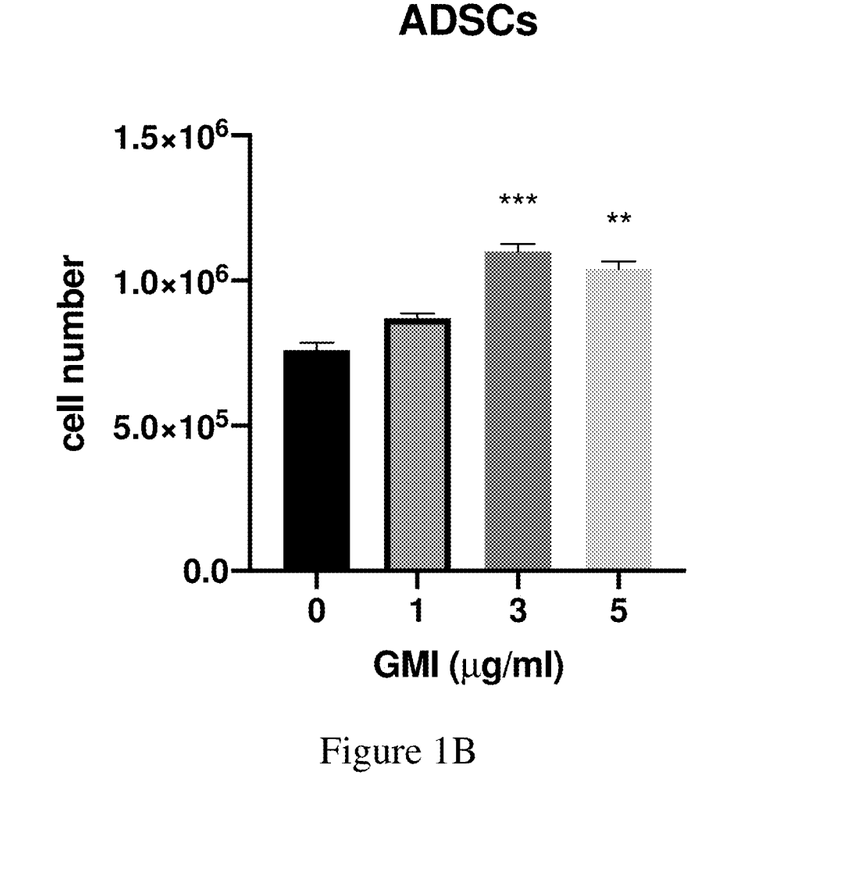

GMI manufactured by Mycomagic Biotechnology Co., Ltd., was used in these examples and it was generated and ameliorated from *Ganoderma microsporum* (see, U.S. Pat. No. 7,601,808, which is incorporated in its entirety for reference). Human adipose-derived stem cells (ADSCs, PT-5006) were purchased from Lonza. Previous studies indicated that GMI could inhibit tumor growth and further induce tumor cell death, but there is no evidence showing the effect of GMI on ADSCs proliferation. In order to figure out the effect of GMI on ADSC proliferation, cell proliferation assay was performed using a hemocytometer. Adipose-derived stem cells ($5\times10^5$ cells) were seeded in a 10 cm petri-dish with mesenchymal stem cell basal medium (American Type Culture Collection, ATCC) containing MSC supplement (2% FBS, 5 ng/ml rhFGF basic, 5 ng/ml rhFGF acidic and 5 ng/ml EGF) and L-Alanyl-L-Glutamine (2.4 mM). After 24 hours of incubation, cells were treated with different concentrations of GMI (0, 1, 3 and 5 μg/ml) for 72 hours. After treatment, cells were harvested by using 1 ml accutase solution and total cell number was counted by a hemocytometer (FIG. 1). Phase contrast images (FIG. 1A) were photographed by a light microscope (magnification, ×100). FIGS. 1A and 1B showed that GMI could significantly induce ADSCs proliferation.

Surface Markers were Consistently Expressed on ADSCs after GMI Treatment

Figure 2:
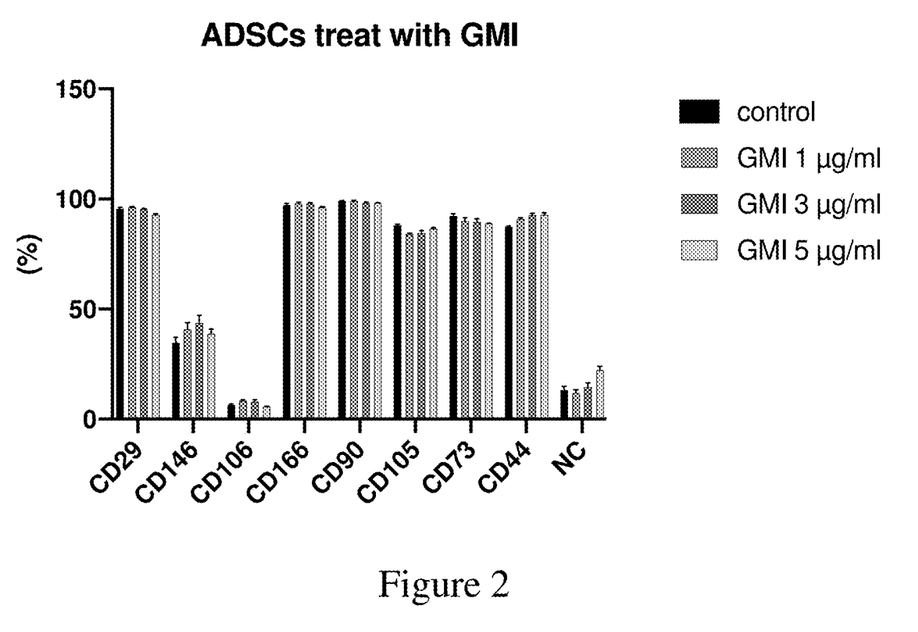
FIG. 2 shows comparison of the expression level of surface markers in ADSCs after GMI treatment. ADSCs ($5\times10^5$ cells) were treated with different concentrations of GMI (0, 1, 3 and 5 µg/ml) for 3 days. After incubation, cells were harvested and stained with specific MSC positive (CD29, CD146, CD166, CD106, CD90, CD105, CD73, CD44) and negative (CD34, CD45, CD11b, CD19, HLA-DR) surface marker antibodies. The results were analyzed by flow cytometry (BD Accuri™ C6 Plus). The experiments were performed in triplicate (n=3).

Antibodies used for flow cytometry analysis, such as anti-CD29-PE (557332), anti-CD146-Alexa Fluor647 (563619), anti-CD166-BB515 (565461), and anti-CD106-Percp-Cy5.5 (563525), were purchased from BD Biosciences. Human MSC analysis Kit (562245) were purchased from BD Biosciences. After cell counting, cells were further analyzed cell surface marker expression level. Control ADSCs and GMI-treated ADSCs were harvested and further stained with anti-CD29, anti-CD106, anti-CD146, anti-CD166, anti-CD90, anti-CD105, anti-CD73, anti-CD44 and negative marker cocktail antibodies for 30 min. After staining, cells were washed with PBS twice and resuspended in 1 ml PBS. Cell surface markers of control cells and GMI-treated cells were assessed by flow cytometry (BD ACCURI™ C6 Plus). Eight MSC-specific surface markers, CD29, CD106, CD146, CD166, CD90, CD105, CD73 and CD44, and five other markers, CD34, CD11b, CD19, CD45 and HLA-DR, were evaluated. As shown in FIG. 2, after GMI treatment, more than 90% of control and GMI-treated ADSCs still expressed MSC-positive markers, such as CD29, CD166, CD90, CD105, CD73 and CD44. Although ADSCs showed lower levels of CD146 and CD106, CD146 and CD106 expressed populations were not affected by GMI treatment. In addition, negative surface markers, such as CD34, CD11b, CD19, CD45 and HLA-DR, on ADSCs were measured by negative control cocktail antibodies. As shown in FIG. 2, MSC negative marker-expressed population was increased after GMI (5 μg/ml) treatment.

Adipogenic and Osteogenic Differentiation Capacity are Preserved in GMI-Treated ADSCs According to FIG. 1, the result showed that GMI could induce ADSC proliferation. In order to figure out whether GMI treatment affects its adipogenic and osteogenic differentiation capacity, ADSCs were treated with different concentrations of GMI (0, 3 and 5 μg/ml) for 3 days. After GMI treatment, ADSCs were harvested and seeded into 24-well plate for adipogenic and osteogenic differentiation assay. Adipogenic and osteogenic differentiation assay were performed by using Mesenchymal Stem Cell Adipogenesis Kit (SCR020) and Mesenchymal Stem Cell Osteogenesis Kit (SCR028, EMD Millipore Corp., MA, USA), respectively. When the cells were 100% confluent, the medium was aspirated from each well and 0.5 ml Adipogenesis Induction medium or Osteogenesis Induction medium was added to the well. Then, the medium was replaced with fresh induction medium every 2-3 days. ADSCs could differentiate into adipocyte or osteocyte after 21 days or 14 days. In adipogenic differentiation assay (FIG. 3A), the medium was aspirated from each well and then the adipocyte was fixed by incubating the adipocyte in 4% paraformaldehyde for 30 min at room temperature. After fixation, each well was rinsed three times with PBS and then rinsed twice with water. The water was removed and Oil Red O solution (0.4 ml/well) was added to the wells. Then, the wells were incubated at room temperature for 50 min. The Oil Red O solution was removed and the wells were rinsed three times with 1 ml water. The resulting cells were stained using hematoxylin solution (0.4 ml/well) for 5 min. Finally, the results were observed by microscope and photographed under a light microscope (magnification, ×400). In osteogenic differentiation assay (FIG. 3B), the medium was aspirated from each well and the osteocyte was fixed by incubating the osteocyte in ice-cold 70% ethanol for 1 hour at room temperature. After fixation, the ethanol was removed and wells were rinsed twice with water for 5 min.

Figure 3A:
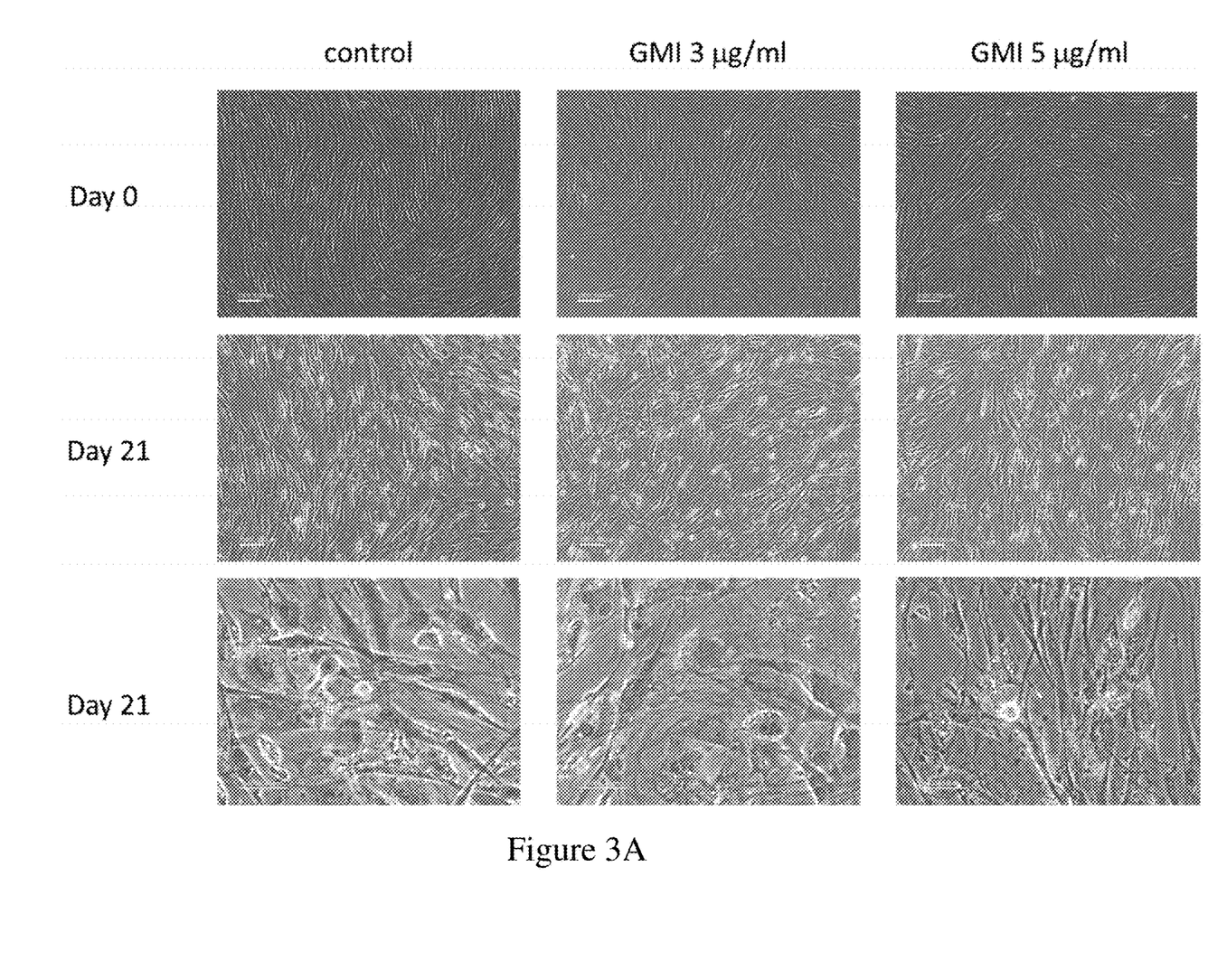
FIGS. 3A and 3B show the capacity of differentiation in control ADSCs or GMI-treated ADSCs. ADSCs were treated with different concentrations of GMI (0, 3 and 5 µg/ml) for 3 days. After treatment, control ADSCs ($6\times10^4$ cells) and GMI-treated ADSCs ($6\times10^4$ cells) were cultured with either adipogenic differentiation media for 21 days (A) or osteogenic differentiation media for 14 days (B). Phase contrast images of ADSCs were photographed at indicated time points. Upper panel and middle panel show cell morphology changed after adipogenic or osteogenic differentiation induction. Lower panel shows the staining results after adipogenic or osteogenic differentiation induction. Scale bar equals 100 mm in osteogenic differentiation and 50 mm in adipogenic differentiation.
Figure 3B:
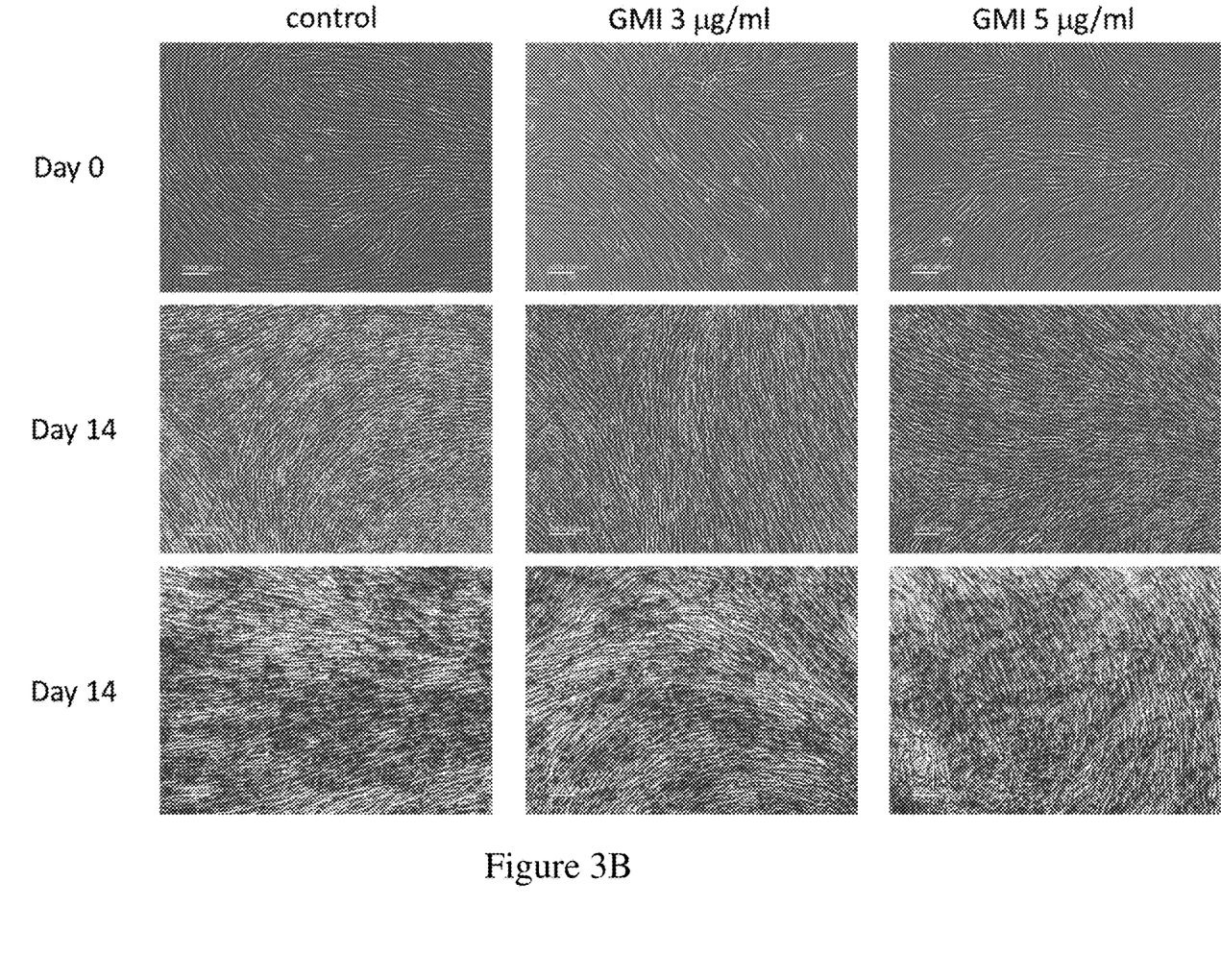

The water was aspirated and Alizarin Red Solution was added to the wells to cover the well (0.5 ml/well). The wells were incubate at room temperature for 30 min. After incubation, the Alizarin Red Solution was removed and the wells were washed four times with 1 ml water. 1 ml water was added to each well to prevent the cells from drying. Finally, the results were observed by microscope and photographed under a light microscope (magnification, ×100). As shown in FIGS. 3A and 3B, ADSCs undergoing adipogenesis not only changed their morphologies to a polygonal or round shape, but also produced abundant lipid droplets in the cytoplasm (shown by red color). On the other hand, ADSCs undergoing osteogenesis showed mineral deposition in the control and GMI-treated cells by Alizarin staining. Based on these observations, GMI-treated ADSCs preserved its adipogenic and osteogenic differentiation capacity.

Example 2

Low Dose GMI Treatment Induces BMSC Proliferation

Figure 4A:
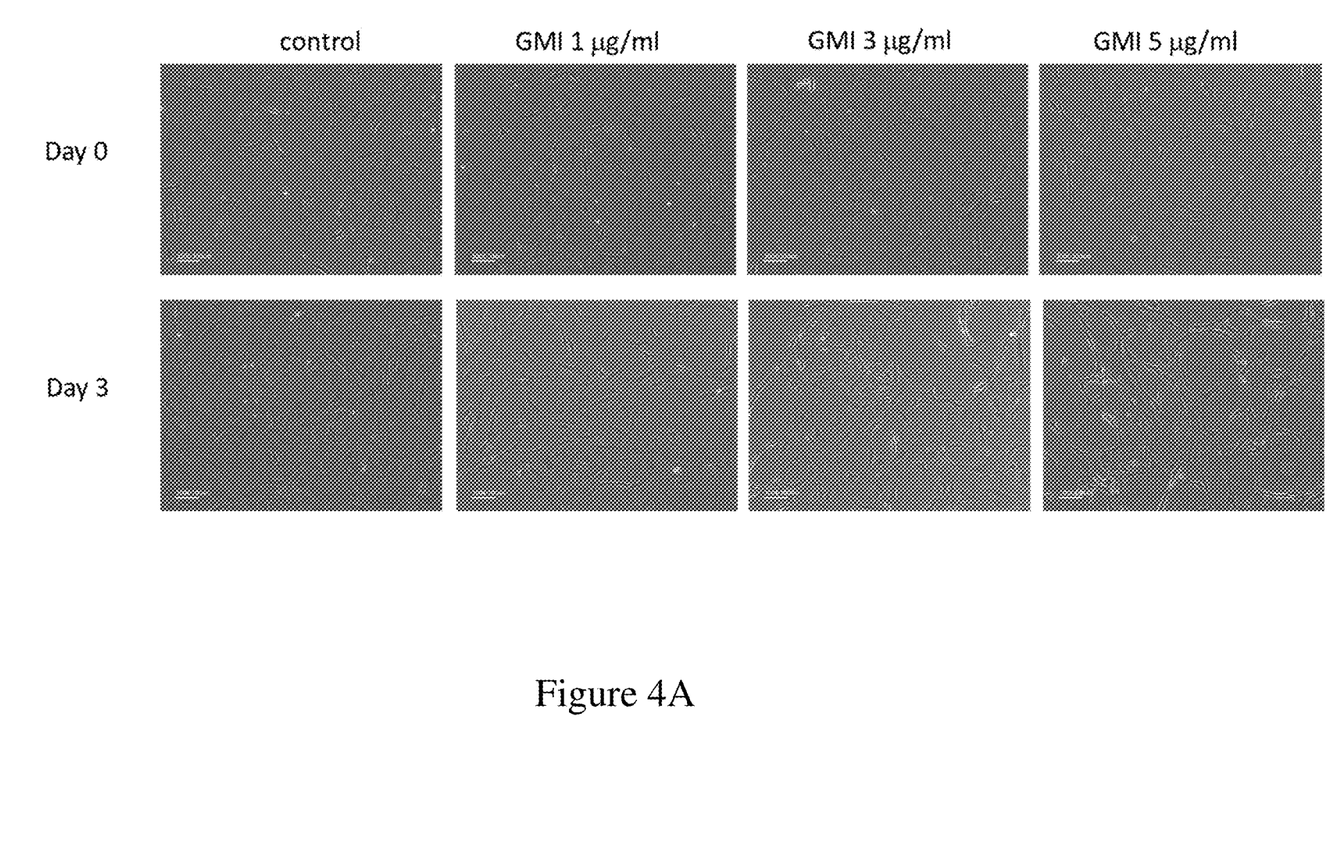
FIGS. 4A and 4B show the effect of GMI on BMSCs proliferation. BMSCs ($2\times10^5$ cells) were treated with different concentrations of GMI (0, 1, 3 and 5 µg/ml) for 3 days. After treatment, cells were harvested, and total cell number was analyzed by a hemocytometer (B). Phase contrast images (A) were photographed by a light microscope. The experiments were performed in triplicate (n=3). *p<0.05 and **p<0.01, versus control cell with no GMI treatment.
Figure 4B:
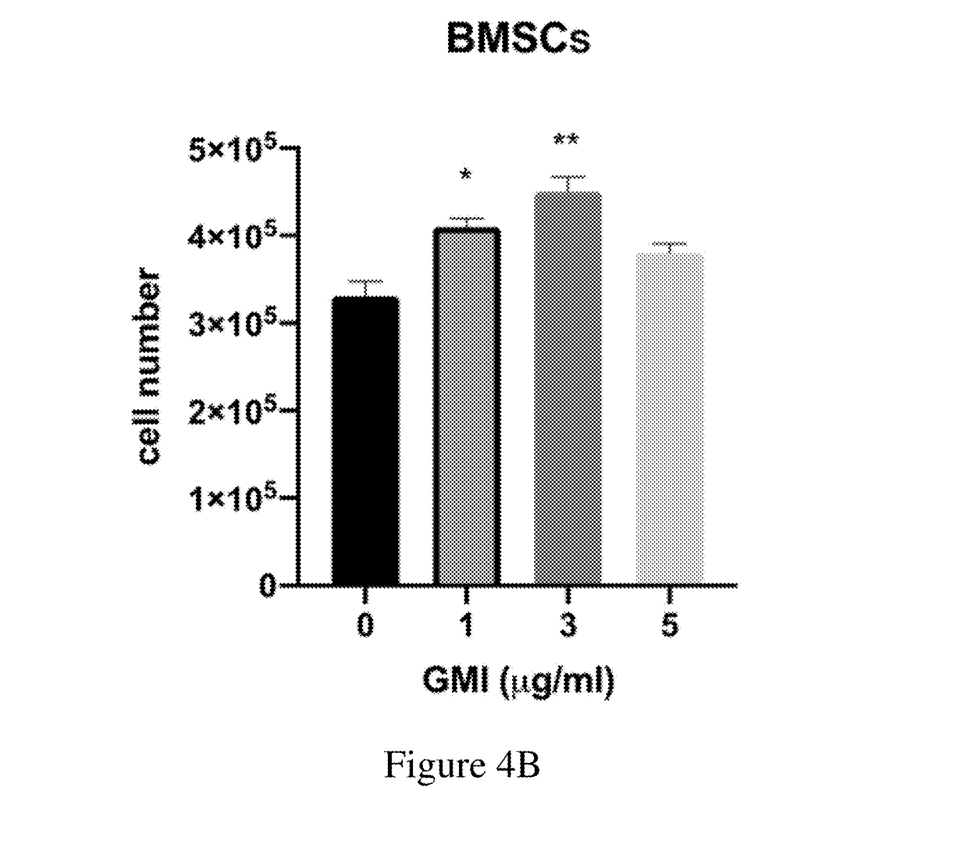

Human bone marrow-derived stem cells (BMSCs) were purchased from ATCC. Cell proliferation assay was performed by using hemocytometer. Previous studies indicated that GMI could inhibit tumor growth and further induce tumor cell death, but there is no evidence showed the effect of GMI on BMSCs proliferation. In order to investigate the role of GMI on BMSCs proliferation, BMSCs ($2 \times 10^5$ cells) were seeded in 10 cm petri-dish with mesenchymal stem cell growth kit (ATCC) containing 7% FBS, 15 ng/ml rhIGF-1, 125 pg/ml rhFGF-b and L-Alanyl-L-Glutamine (2.4 mM). After 24 hours incubation, cells were treated with different concentrations of GMI (0, 1, 3 and 5 µg/ml) for 72 hours. After treatment, cells were harvested by using accutase and cell number was counted by a hemocytometer (FIG. 4B). Phase contrast images (FIG. 4A) were photographed by a light microscope (magnification, ×100). FIGS. 4A and 4B showed that GMI could significantly induce BMSCs proliferation.

Surface Markers were Consistently Expressed on BMSCs after GMI Treatment

Figure 5:
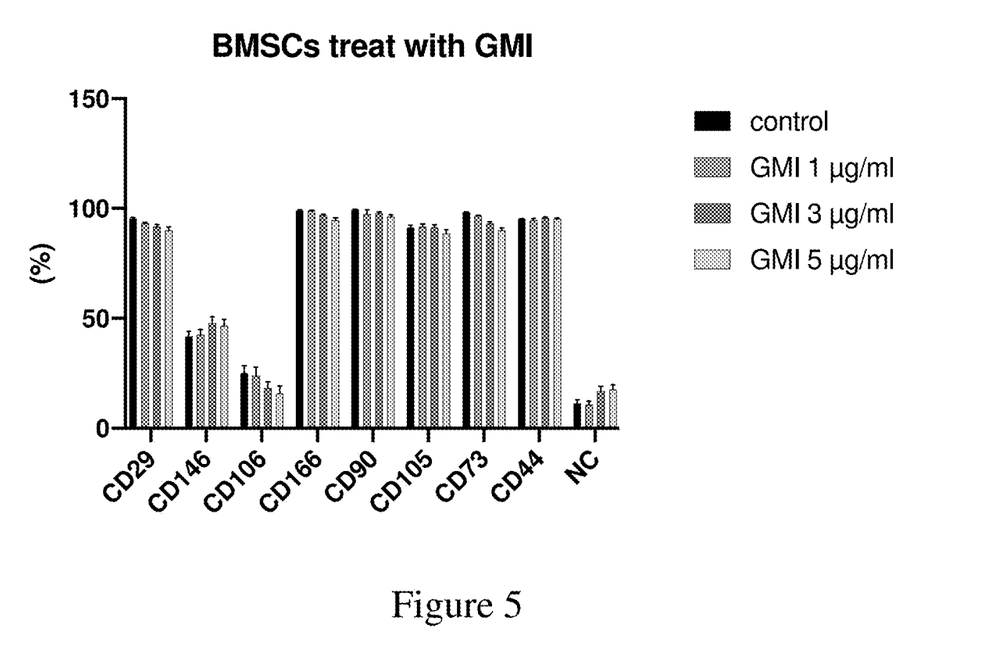
FIG. 5 shows comparison of the expression level of surface markers in BMSCs after GMI treatment. BMSCs ($2\times10^5$ cells) were treated with different concentrations of GMI (0, 1, 3 and 5 µg/ml) for 3 days. After incubation, cells were harvested and stained with specific MSC positive (CD29, CD146, CD166, CD106, CD90, CD105, CD73, CD44) and negative (CD34, CD45, CD11b, CD19, HLA-DR) surface marker antibodies. The results were analyzed by flow cytometry (BD Accuri™ C6 Plus). The experiments were performed in triplicate (n=3).

Antibodies used for flow cytometry analysis, such as anti-CD29-PE (557332), anti-CD146-Alexa Fluor647 (563619), anti-CD166-BB515 (565461), and anti-CD106-Percp-Cy5.5 (563525), were purchased from BD Biosciences. Human MSC analysis Kit (562245) were purchased from BD Biosciences. After cell counting, cells were further analyzed cell surface marker expression level. Control BMSCs and GMI-treated BMSCs were stained with anti-CD29-PE, anti-CD106-Percp-Cy5.5, anti-CD146-Alexa Fluor647, anti-CD166-BB515, anti-CD90-FITC, anti-CD105-Percp-Cy5.5, anti-CD73-APC, anti-CD44-PE and PE-labeled negative marker cocktail antibodies for 30 min. After staining, cells were washed with PBS twice and resuspended in 1 ml PBS. Cell surface markers of control and GMI-treated cells were assessed by flow cytometry (BD ACCURI™ C6 Plus). Eight MSC-specific surface markers, CD29, CD106, CD146, CD166, CD90, CD105, CD73 and CD44, and five other markers, CD34, CD11b, CD19, CD45 and HLA-DR, were evaluated. As shown in FIG. 5, after GMI treatment, more than 90% of control and GMI-treated BMSCs still expressed MSC-positive markers, such as CD29, CD166, CD90, CD105, CD73 and CD44. Although BMSCs showed lower levels of CD146 and CD106, CD146 and CD106 expressed populations were not affected by GMI treatment. In addition, negative surface markers, such as CD34, CD11b, CD19, CD45 and HLA-DR, on BMSCs were measured by negative control cocktail antibodies. As shown in FIG. 5, MSC negative marker-expressed population was increased after GMI (5 µg/ml) treatment.

Figure 6A:
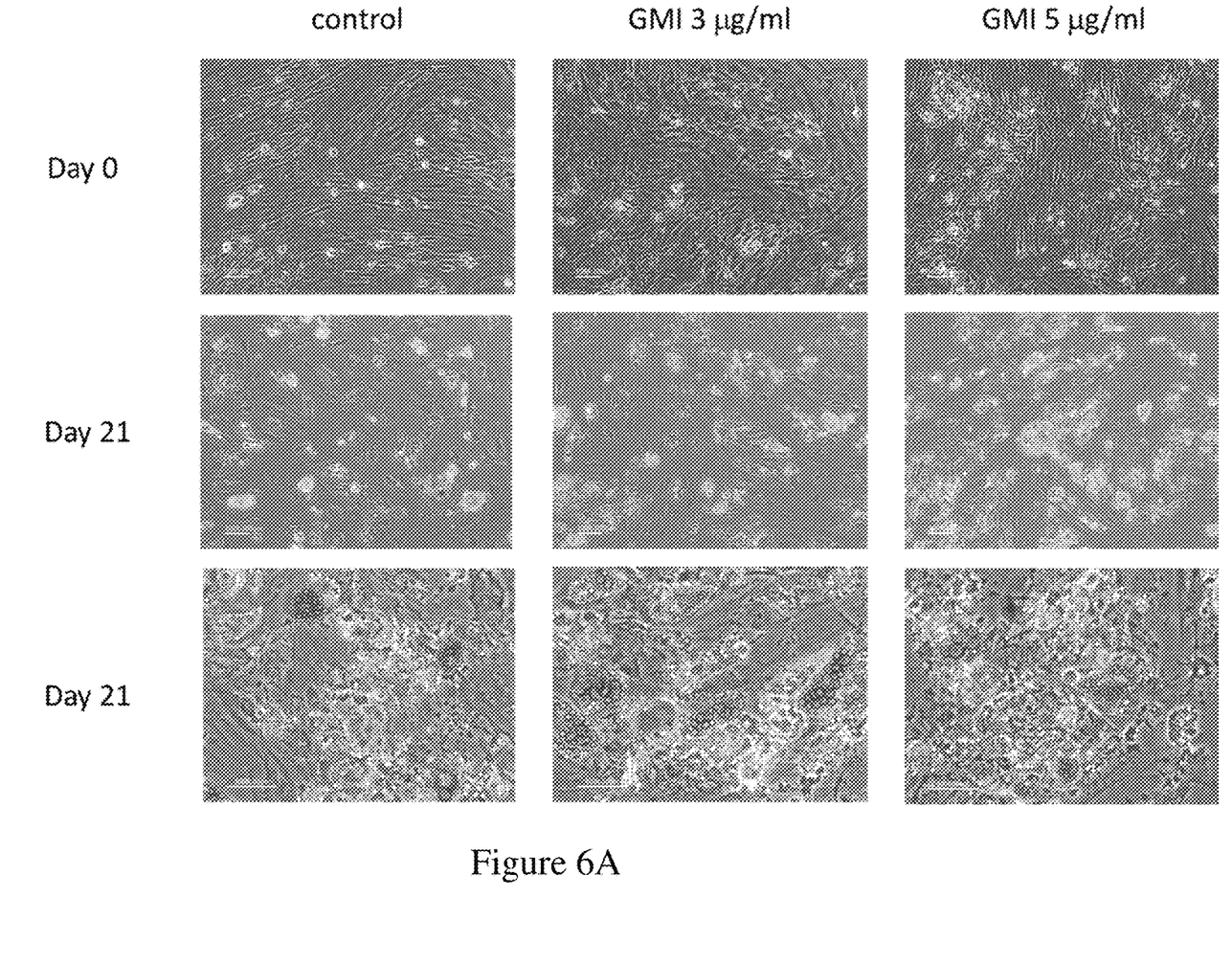
FIGS. 6A and 6B show the capacity of differentiation in control BMSCs or GMI-treated BMSCs. BMSCs were treated with different concentration of GMI (0, 3 and 5 µg/ml) for 3 days. After treatment, control BMSCs ($6\times10^4$ cells) and GMI-treated BMSCs ($6\times10^4$ cells) were cultured with either adipogenic differentiation media for 21 days (A) or osteogenic differentiation media for 14 days (B). Phase contrast images of BMSCs were photographed at indicated time points. Upper panel and middle panel show cell morphology changed after adipogenic or osteogenic differentiation induction. Lower panel shows the staining results after adipogenic or osteogenic differentiation induction. Scale bar equals 100 mm in osteogenic differentiation photos and 50 mm in adipogenic differentiation photos.
Figure 6B:
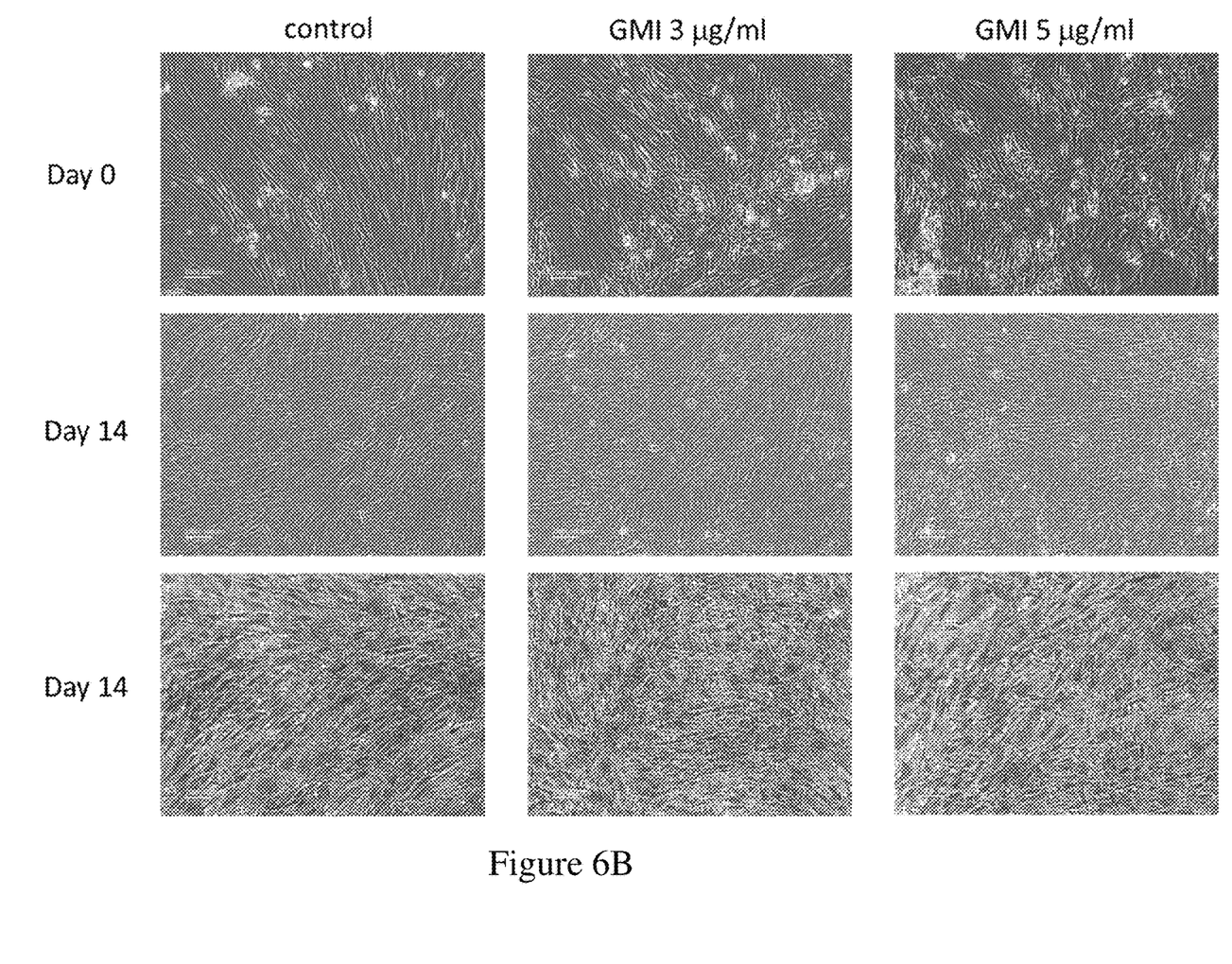

Adipogenic and Osteogenic Differentiation Capacity are Preserved in GMI-Treated BMSCs According to FIG. 4, GMI could induce BMSCs proliferation. In order to figure out whether GMI-induced BMSCs proliferation affects its adipogenic and osteogenic differentiation capacity, adipogenic and osteogenic differentiation assays were performed. BMSCs were treated with different concentrations of GMI (0, 3 and 5 µg/ml) for 3 days. After GMI treatment, BMSCs were harvested and seeded into a 24-well plate for adipogenic and osteogenic differentiation assays. Adipogenic and osteogenic differentiation assays were performed using Mesenchymal Stem Cell Adipogenesis Kit and Mesenchymal Stem Cell Osteogenesis Kit (EMD Millipore Corp., MA, USA), respectively. When the cells are 100% confluent, the medium was aspirated from each well and 0.5 ml Adipogenesis Induction medium or Osteogenesis Induction medium was added to the wells. The medium was replaced with fresh induction medium every 2-3 days. BMSCs could differentiate into adipocyte or osteocyte after 21 days or 14 days of induction. In adipogenic differentiation assay (FIG. 6A), the medium was aspirated from each well and then adipocyte was fixed by incubating the adipocyte in 4% paraformaldehyde for 30 min at room temperature. After fixation, each well was rinsed three times with PBS and then rinsed twice with water. The water was aspirated and Oil Red O solution (0.4 ml/well) was added to the wells. The wells were incubated at room temperature for 50 min. After incubation, the Oil Red O solution was removed and the wells were rinsed three times with 1 ml water. The cell nucleus were stained using hematoxylin solution (0.4 ml/well) for 5 min. Then, the cells were observed by microscope and photographed under a light microscope (magnification, ×400). In osteogenic differentiation assay (FIG. 6B), the medium was aspirated from each well and the osteocyte was fixed by incubating in ice-cold 70% ethanol for 1 hour at room temperature. After fixation, the ethanol was removed and the wells were rinsed twice with water for 5 min. The water was aspirated and Alizarin Red Solution was added to cover the well (0.5 ml/well). The wells were incubated at room temperature for 30 min. After incubation, the Alizarin Red Solution was removed and wash the well four times with 1 ml water. Add 1 ml water to each well to prevent the cells from drying. Finally, the results were observed by microscope and photographed under a light microscope (magnification, ×100). As shown in FIGS. 6A and 6B, BMSCs undergoing adipogenesis not only changed their morphologies to a polygonal or round shape, but also produced abundant lipid droplets in the cytoplasm (shown in red). On the other hand, BMSCs undergoing osteogenesis showed mineral deposition in the control and GMI-treated cells by Alizarin staining. FIG. 6 showed that GMI-treated BMSCs preserved adipogenic and osteogenic differentiation capacity.

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method for proliferating or propagating undifferentiated stem cells, comprising contacting a population of stem cells with an effective amount of a *Ganoderma* immunomodulatory protein or an effective fragment thereof
   wherein the *Ganoderma* immunomodulatory protein comprises an amino acid sequence as the amino acid sequence set forth in any one of SEQ ID NO: 3 and SEQ ID NO: 4; the effective fragment of *Ganoderma* immunomodulatory protein comprises an amino acid sequence set forth in any one of SEQ ID NO: 1 and SEQ ID NO: 2; and
   wherein the stem cells comprise embryonic stem cells, mesenchymal stem cells (MSC), or tissue-specific stem cells.

2. The method of claim 1, wherein the stem cells remain undifferentiated after the propagation.

3. The method of claim 1, wherein the *Ganoderma* immunomodulatory protein comprises an amino acid sequence of SEQ ID NO: 3.

4. The method of claim 1, wherein the *Ganoderma* immunomodulatory protein comprises an amino acid sequence of SEQ ID NO: 4.

5. The method of claim 1, wherein an amino acid sequence of the effective fragment of *Ganoderma* immunomodulatory protein is selected from the group consisting of SEQ ID NO: 1 and SEQ ID NO: 2.

6. The method of claim 1, wherein the effective amount of the *Ganoderma* immunomodulatory protein or the effective fragment thereof is less than 15 μg/mL.

7. The method of claim 1, wherein the effective amount of the *Ganoderma* immunomodulatory protein or the effective fragment thereof is less than 12.5 μg/mL.

8. The method of claim 1, wherein the effective amount of the *Ganoderma* immunomodulatory protein or the effective fragment thereof ranges from about 1.0 μg/mL to about 15 μg/mL.

9. The method of claim 1, wherein the effective amount of the *Ganoderma* immunomodulatory protein or the effective fragment thereof ranges from about 1.5 μg/mL to about 12.5 μg/mL.

10. The method of claim 1, wherein the effective amount of the *Ganoderma* immunomodulatory protein or the effective fragment thereof ranges from about 1.5 μg/mL to about 6.5 μg/mL.

11. The method of claim 1, wherein the population of the stem cells is of human origin.

12. The method of claim 1, wherein the mesenchymal stem cells are adipose tissue-derived mesenchymal stem cells or bone marrow-derived mesenchymal stem cells.

* * * * *